(12) United States Patent
Geyer

(10) Patent No.: US 7,214,216 B2
(45) Date of Patent: May 8, 2007

(54) DRAINAGE CHAMBER FOR COLLECTING BODY FLUIDS, IN PARTICULAR LIQUOR

(76) Inventor: Marco Geyer, Jungfrauenthal 26, D-20149 Hamburg (DE)

( * ) Notice: Subject to any disclaimer, the term of this patent is extended or adjusted under 35 U.S.C. 154(b) by 0 days.

(21) Appl. No.: 11/107,298

(22) Filed: Apr. 15, 2005

(65) Prior Publication Data
US 2005/0234429 A1    Oct. 20, 2005

(30) Foreign Application Priority Data
Apr. 17, 2004    (DE) ................ 20 2004 006 070 U

(51) Int. Cl.
*A61M 1/00*    (2006.01)
(52) U.S. Cl. .................... 604/324; 604/323; 604/321
(58) Field of Classification Search ............. 604/319, 604/321, 320, 326, 324, 355, 356, 323, 541
See application file for complete search history.

(56) References Cited

U.S. PATENT DOCUMENTS

| | | | | |
|---|---|---|---|---|
| 2,936,757 A | * | 5/1960 | Trace | 604/321 |
| 3,345,980 A | * | 10/1967 | George | 600/575 |
| 3,571,822 A | * | 3/1971 | Shaw, Jr. | 4/213 |
| 3,661,143 A | * | 5/1972 | Henkin | 600/575 |
| 3,888,126 A | * | 6/1975 | Cross | 73/426 |
| 4,000,649 A | * | 1/1977 | Hanifl | 600/575 |
| 4,015,960 A | * | 4/1977 | Nutter | 55/355 |
| 4,291,706 A | * | 9/1981 | Voges et al. | 600/575 |
| 4,319,573 A | * | 3/1982 | Whitlock | 604/328 |
| 4,465,483 A | * | 8/1984 | Weilbacher | 604/317 |
| 4,540,413 A | * | 9/1985 | Russo | 604/320 |
| 4,664,660 A | * | 5/1987 | Goldberg et al. | 604/321 |
| 4,767,417 A | * | 8/1988 | Boehringer et al. | 604/31 |
| 4,870,975 A | * | 10/1989 | Cronk et al. | 600/562 |
| 4,902,284 A | * | 2/1990 | D'Antonio et al. | 604/320 |
| 4,945,580 A | * | 8/1990 | Schmitt et al. | 4/325 |
| 4,955,873 A | * | 9/1990 | Rajlevsky | 604/322 |
| 4,955,921 A | * | 9/1990 | Basile et al. | 4/354 |
| 4,974,263 A | * | 12/1990 | Sheppard et al. | 4/250 |
| 4,988,342 A | * | 1/1991 | Herweck et al. | 604/321 |
| 5,005,226 A | * | 4/1991 | Basile et al. | 4/354 |
| 5,023,960 A | * | 6/1991 | Ratanagsu | 4/393 |
| 5,026,358 A | * | 6/1991 | Everett et al. | 604/320 |
| 5,029,346 A | * | 7/1991 | Fernald, Sr. | 4/213 |

(Continued)

FOREIGN PATENT DOCUMENTS

DE    197 20 933    1/1998

(Continued)

*Primary Examiner*—Tatyana Zalukaeva
*Assistant Examiner*—Paula L. Craig
(74) *Attorney, Agent, or Firm*—Friedrich Kueffner

(57) ABSTRACT

A drainage chamber for collecting body fluids, in particular liquor, includes a collecting area limited by an outer wall for collecting the body fluid, an inlet connection linked to the collecting area for linking to a drainage catheter (an intra-ventricular catheter), an outlet connection and a ventilation connection linked to the environment. The drainage chamber has a spring-loaded first closing element, biased in the direction of a first closing position, which in its closing position closes both the inlet connection and the ventilation connection and which is displaceable against the spring tension by means of an actuating mechanism into an open position, in which it releases the inlet connection and the ventilation connection.

13 Claims, 1 Drawing Sheet

U.S. PATENT DOCUMENTS

| | | | | |
|---|---|---|---|---|
| 5,035,011 | A * | 7/1991 | Rozenblatt et al. | 4/665 |
| 5,040,246 | A * | 8/1991 | Zanino | 4/225.1 |
| 5,046,201 | A * | 9/1991 | Steinhardt et al. | 4/354 |
| 5,084,035 | A * | 1/1992 | Salvadori et al. | 604/323 |
| 5,100,376 | A * | 3/1992 | Blake, III | 604/6.1 |
| 5,114,416 | A * | 5/1992 | Karwoski et al. | 604/321 |
| 5,154,712 | A * | 10/1992 | Herweck et al. | 604/321 |
| 5,207,661 | A * | 5/1993 | Repschlager | 604/317 |
| D340,285 | S * | 10/1993 | Herweck et al. | D24/169 |
| 5,286,262 | A * | 2/1994 | Herweck et al. | 604/321 |
| 5,300,050 | A * | 4/1994 | Everett et al. | 604/320 |
| 5,318,510 | A * | 6/1994 | Cathcart | 604/6.09 |
| 5,397,299 | A * | 3/1995 | Karwoski et al. | 604/6.1 |
| 5,401,262 | A * | 3/1995 | Karwoski et al. | 604/321 |
| 5,472,605 | A * | 12/1995 | Zuk, Jr. | 210/436 |
| RE35,225 | E * | 4/1996 | Herweck et al. | 604/321 |
| 5,507,734 | A * | 4/1996 | Everett et al. | 604/320 |
| 5,722,964 | A * | 3/1998 | Herweck et al. | 604/317 |
| 5,779,902 | A * | 7/1998 | Zuk, Jr. | 210/436 |
| 5,807,358 | A * | 9/1998 | Herweck et al. | 604/320 |
| 5,865,408 | A * | 2/1999 | Swisher et al. | 248/188.1 |
| 5,908,403 | A * | 6/1999 | Bosma et al. | 604/43 |
| D430,286 | S * | 8/2000 | Valerio et al. | D24/108 |
| 6,250,482 | B1 * | 6/2001 | Want et al. | 211/181.1 |
| 6,280,429 | B1 * | 8/2001 | Lewis et al. | 604/406 |
| 6,358,218 | B1 * | 3/2002 | Want et al. | 600/573 |
| 6,368,310 | B1 * | 4/2002 | Bemis et al. | 604/319 |
| 6,371,947 | B1 * | 4/2002 | Gibertoni | 604/320 |
| 6,391,009 | B1 * | 5/2002 | Dorado | 604/319 |
| 6,478,774 | B1 * | 11/2002 | Balugani et al. | 604/151 |
| 6,482,190 | B1 * | 11/2002 | Genese et al. | 604/327 |
| 6,632,203 | B2 * | 10/2003 | Swisher et al. | 604/317 |
| 6,923,424 | B2 * | 8/2005 | Maercovich et al. | 251/30.01 |
| 6,981,285 | B2 * | 1/2006 | Sigler et al. | 4/434 |
| 2001/0041857 | A1 * | 11/2001 | Sansoucy | 604/33 |
| 2003/0017791 | A1 * | 1/2003 | Mizuno | 451/60 |

FOREIGN PATENT DOCUMENTS

DE      299 06 246      9/1999

* cited by examiner

DRAINAGE CHAMBER FOR COLLECTING BODY FLUIDS, IN PARTICULAR LIQUOR

BACKGROUND OF THE INVENTION

1. Field of the Invention

The invention relates to a drainage chamber for collecting body fluids, in particular liquor, with a collecting area limited by an outer wall for collecting the body fluid and with an inlet connection linked to the collecting area for linking to a drainage catheter, an outlet connection and a ventilation connection.

2. Description of the Related Art

In patients who produce too much liquor, to maintain a "healthy" internal pressure of the skull, excess liquor must be drained off. Liquor drainage systems are currently used for this. These systems usually contain, among other things, a drainage chamber (alternatively a drainage bag), in which the drained-off liquor is collected and which is suspended at a preset height above the patient's skull to set the desired internal pressure of the skull. Leading into this drainage chamber is an inlet connection, which is linked via a hose conduit to a drainage catheter (intraventricular catheter), which reaches into the patient's ventricular system to remove liquor. On the chamber there is further an outlet connection, which can be opened as required, in order to allow liquor which has collected in the chamber to flow out into a drainage bag normally linked to this connection. The drainage chamber further has a ventilation connection, through which air can escape when the drainage chamber is being filled with liquor and air can flow back when the liquor is let into the drainage bag. In order to prevent infection of the system, a filter is placed on the ventilation connection, which has a sufficiently small pore width to hold back germs.

In the known systems, hose clips and shut-off taps are used to close the inlet, the outlet and the ventilation connections or conduits. With these, a flexible hose, connected to the respective connection, is clamped or closed in such a way that passage is no longer possible. In normal operation the drainage chamber is in a holder or receptacle at a particular height above the patient's head and the inlet connection and the ventilation connection are open. The outlet connection, on the other hand, is closed.

If the patient has to change beds or has to be moved in some other way, it is regularly necessary to take the drainage chamber out of its receptacle and to place it on the patient's bed, for example, during work on the patient. Before this can be done, it is essential that the inlet connection and also the ventilation connection are closed, so that, on the one hand, no fluctuations in pressure in the liquor system in the patient's skull arise because of the change in height of the drainage chamber and, on the other hand, any contact of liquor with the filter is ruled out. The proteins or blood particles contained in the liquor may otherwise glue up or block the filter membrane, both of which may entail a risk to the patient. For if the filter is glued up air can no longer escape through it out of the drainage chamber and a counterpressure builds up which may lead to an increase in pressure in the patient's skull with corresponding consequences. Consequences of this kind are particularly critical in children, in particular young children and babies, as patients, as they react particularly sensitively to fluctuations in pressure, owing to the smaller amount of liquor by nature. Furthermore, there may be a "siphon effect" where the chamber is emptied because the filter is glued up or closed.

Correct operation of the clamps by the care staff is therefore extremely important and a possible source of error with fatal consequences. If, as frequently provided, further connections are provided in the conduit to the drainage catheter (intraventricular catheter) for administering medicines or measuring pressure, here too three-way valves integrated in the system at these points must be correctly operated, further increasing the possibility of defective operation.

SUMMARY OF THE INVENTION

Against this background the object of the present invention is to further develop a previously known drainage chamber to the effect that it becomes easier to operate and that, in particular, the operating errors alluded to above can be avoided.

In accordance with the present invention this object is met by a drainage chamber for collecting body fluids, in particular liquor, with a collecting area limited by an outer wall for collecting the body fluid and with an inlet connection linked to the collecting area for linking to a drainage catheter (an intraventricular catheter), an outlet connection and a ventilation connection linked to the environment, characterised in that it has a spring-loaded first closing element, biased in the direction of a first closing position, which, in its closing position, closes both the inlet connection and the ventilation connection and which is displaceable against the spring tension by means of an actuating mechanism into an open position, in which it releases the inlet connection and the ventilation connection.

The present invention may also provide a combination of a new drainage chamber and a receptacle, with which the above-mentioned problem can likewise be solved.

By means of the first closing element provided according to the invention in the drainage chamber, on the one hand, both the inlet connection and the ventilation connection are closed or opened in one operating cycle. On the other hand, the spring loading of the first closing element serves to ensure that this closing element moves into the closing position in normal circumstances. Not until it is opened and secured against the spring loading is the drainage chamber ready for operation with open inlet connection and ventilation connection. A closing element in the sense of this invention, is also to be understood as a closing device composed of several elements, as long as it guarantees the above-described function.

Advantageously, the first closing element has an actuating device which cooperates with a receptacle for the drainage chamber. In this way, when the chamber is inserted into the receptacle, the first closing element is "automatically" opened and the inlet and ventilation connections, which need to be opened for smooth functioning of the drainage chamber, are released. When the drainage chamber is removed from the receptacle, on the other hand, said connections are "automatically" closed again by the spring force, as safe handling of the chamber demands.

The further development of the drainage chamber leads to the inlet connection being guided via the pipe conduit into the part of the collecting area at the top in the functional position of the drainage chamber. This additionally helps to prevent the liquor running back if there is a defect in the closing element.

In combination with the above features, the ventilation connection may be arranged on the wall of the drainage chamber located at the top in the functional position thereof, and may be linked to a tubular extension running downwards, which reaches into the collecting area at least to the height of the mouth of the pipe conduit. A closing bar, arranged diagonally in the collecting area and biased by a spring into a closing position, may be provided as first closing element, which, on actuation, at the same time releases or closes the pipe conduit and the tubular extension. This gives a simple implementation of a first closing element.

Integration of a filter into the outer wall gives a compact drainage chamber in which additionally there is no need for subsequent connection of a filter with the risk of germs entering the system. The filter is configured in its porosity in such a way that it can safely filter out germs from the air flowing in through the ventilation connection, without interfering too much with the air flow.

A link of the ventilation connection to the outlet connection, via a conduit provided with a ventilation/overflow orifice, yields the advantage that this conduit can be simultaneously used as an overflow for an over-full drainage chamber.

A second closing element, for opening or closing the outlet connection, helps to prevent this connection being left open accidentally after the liquor has been let out of the collecting area. Only when the closing element is displaced against the spring force is the outlet connection released. Otherwise, it remains closed by the second closing element biased into the closing position by the spring force. With this second closing element, at the same time as the outlet connection is opened, the inlet connection is closed to prevent liquor being extracted from the patient's skull when the liquor flows out of the drainage chamber, owing to a thereby arising suction effect.

The second closing element can be constructed analogously to the first in a simple manner as a closing bar.

Encapsulation, of the first or the first and second closing element, against contact with the liquor, serves to prevent germs entering the system and, ultimately, the patient's skull and, therefore, possible infections.

A drainage chamber with an outer wall made of a transparent material allows the hospital staff to observe the drained-off liquor and to make diagnoses. For example, an increased blood content in the liquor or similar may be established. Additionally, the transparent outer wall may have markings for reading the volume of liquor in the collecting area.

A germicidal coating of the inside of the outerwall nevertheless kills any germs which may have entered the system.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

BRIEF DESCRIPTION OF THE DRAWING

In the drawing:
The single FIGURE of the drawing is a schematic side view.

DETAILED DESCRIPTION OF THE INVENTION

Figure 1:
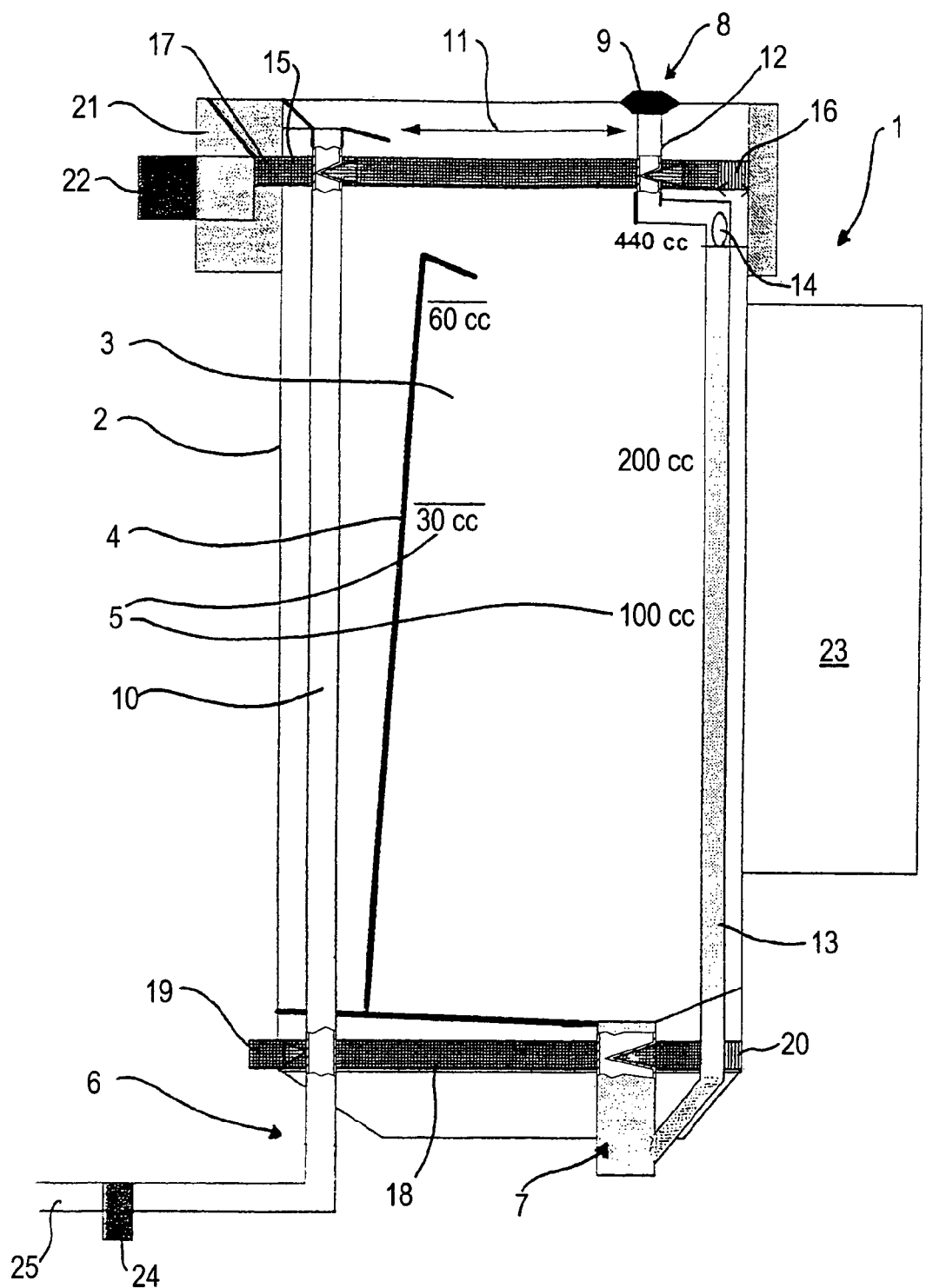

In the FIGURE a drainage chamber 1 is illustrated in a schematic side view. The drainage chamber 1 has a collecting area 3, enclosed by a rigid, transparent outer wall 2. The outer wall 2 is coated with silver oxide on its inner side in contact with the collecting area 3. This material serves to kill off any germs possibly in the collecting area. In the collecting area 3 is arranged an intermediate wall 4 which divides the collecting area into two sections of different volumes. On the outer wall 2, in the area of the section of smaller volume and in the area of the section of larger volume respectively, a scale 5 is applied, indicating the contents located in the collecting area 3 in cubic centimetres.

Arranged on the drainage chamber 1 are further an inlet connection 6, an outlet connection 7 and a ventilation connection 8, the functioning of which will be explained in greater detail later.

The ventilation connection 8 is covered by a filter 9 permanently integrated in the outer wall 2 of the drainage chamber 1, which has a porosity which is suitable for holding back germs contained in the air.

The inlet connection 6 passes into a pipe conduit 10 penetrating the outer wall 10 2 in an area at the bottom in a functional position of the drainage chamber and guided inside the collecting area 3 as far as the end of the drainage chamber 1 located at the top in the functional position. At the upper end, the pipe conduit 10 is open and this end is above the section of smaller volume closed off by the intermediate wall 4. The level at which the orifice of the pipe conduit 10 is located is indicated by a double arrow, designated as a pressure level 11.

On the far side of the filter 9, a tubular extension 12 extends into the interior of the collecting area 3, starting from the ventilation connection 8. This tubular extension passes into a conduit 13, which runs downwards inside the collecting area 3 (seen in functional position of the drainage chamber 1) and is there linked to the outlet connection 7. In the conduit 13 an overflow/ventilation orifice 14 is arranged, which links the conduit 13 to the collecting area 3.

A closing bar 15 crossing the collecting area 3 is arranged at the end of the drainage chamber 1 at the top in the functional position. This is encapsulated against the collecting area 3 and has means for closing the inlet connection 6 (or the pipe conduit 10) and the ventilation connection 8 (or the tubular extension 12). The closing bar 15 is biased by a spring 16 in the direction of a closing position in which it closes both the inlet connection 6 and the ventilation connection 8. The closing bar 15 protrudes with a projection 17 beyond the outer wall 2. This projection 17 serves to actuate the closing bar 15 for displacing thereof out of the closing position and against the spring force of the spring 16 into an open position, in which both the inlet connection 6 and the ventilation connection 8 are released, i.e. linked to the collecting area 3.

A further closing bar 18 is arranged in the area of the collecting area 3 at the bottom in the functional position of the drainage chamber 1. This closing bar 18 is also encapsulated against the collecting area. It has means with which it can close or release the inlet connection 6, more precisely the pipe conduit 10, and the outlet connection 7. The closing bar 18 also protrudes with a projection 19, which serves as an actuating element, beyond the outer wall 2. A spring 20 biases the closing bar 18 into a closing position in which it closes the outlet connection 7 and releases the inlet connection 6. If the projection 19 is pressed against the spring force of the spring 20 in the direction of the outer wall 2, the closing bar 18 closes the inlet connection 6 and releases the outlet connection 7.

The drainage chamber 1 is suspended for use in a receptacle 21, which in turn is on its part arranged on a tripod, for example. Arranged on the receptacle 21 is a trigger 22 with which the closing bar 15 can be actuated, in a way which will be described in greater detail later.

To the side of the drainage chamber 1 in this embodiment example a trade mark slip 23 is also arranged, on which product information and in particular brief instructions can be printed.

Finally, another section of a supply line 25 linked to the supply line connection can be seen, in which a pressure measuring connection 24 for a pressure transducer is arranged.

The drainage chamber 1 is used as follows.

The supply line 25, which leads to an intraventricular catheter in the patient's skull, is linked to the supply line connection 6. All the time the drainage chamber 1 is not inserted into the receptacle 21 or the projection 17 of the closing bar 15 is not pressed against the spring force of the spring 16, the supply line connection 6 and the ventilation connection 8 are closed. The drainage chamber 1 is then inserted into the receptacle 21 fixed to a tripod or similar. By cooperation between a stop face in the receptacle 21 and the projection 17, the latter is pressed against the force of the spring 16 in the direction of the outer wall 2 and the closing bar 15 is moved into the open position. In other words, simply by inserting the drainage chamber 1 into the receptacle 21, and thus to a certain extent automatically, the inlet connection 6 and the ventilation connection 8 are opened, and therefore linked to the collecting area 3.

Now liquor can flow out of the patient's skull into the collecting area 3 through the supply line 25 via the inlet connection 6 or the pipe conduit 10. The hydrostatic pressure desired as liquor pressure in the skull is set by setting the relative height difference between the level of the patient's head and the pressure level 11. The liquor emerges from the orifice of the pipe conduit 10 and first arrives in the section of the collecting area with the smaller volume. Here a volume of liquor can be more accurately read owing to the finer scaling. If the volume of liquor in the collecting area exceeds the amount which can be accommodated in this section, it overflows at the upper edge of the intermediate wall 4 and arrives in the further section which it then likewise fills. While the collecting area 3 is filling up with liquor, air escapes via the overflow/ventilation orifice 14 and the tubular extension through the filter 9 on the ventilation connection 8.

If the maximum filling height of the collecting area is exceeded, liquor emerges 10 via the overflow/ventilation orifice 14 and via the conduit 13 goes past the closing bar 18 to the outlet connection 7 and from there into an adjoining drainage bag.

If the drainage chamber 1 has to be removed from the receptacle 21 and placed on the patient's bed, for example, because the patient has to change beds, for example, it is not necessary to close the various conduits "by hand". If, namely, the drainage chamber 1 is removed from the receptacle 21, the projection 17 is released again and the spring 16 presses the closing bar 15 into the closed position in which it closes the inlet connection 6 and the ventilation connection 8.

In that the outer wall 2 is rigid, no pressure can be built up in the drainage chamber 1 even owing to accidental loading thereof, which could lead to unwanted escape of liquor in spite of closed inlet 6 and ventilation 8 connections. If a measurement of the liquor pressure in the patient's skull is to be performed via a pressure sensor connected to the pressure measuring connection 24, in order not to adulterate this measurement, the inlet connection 6 (and also the ventilation connection 8) is closed. The trigger 22 is provided for this in the receptacle. If it is actuated, the projection 17 of the closing bar 15 is released and the spring 16 presses the latter into the closing position.

For selective letting off of liquor via the outlet connection 7 into a drainage bag attached thereto, the projection 19 of the closing bar 18 at the bottom in the functional position of the drainage chamber 1, is pressed against the spring force of the spring 20 and in the direction of the outer wall 2. In this way the inlet connection 6 (or the pipe conduit 10) is closed and at the same time the outlet connection 7 is opened. (Filtered) air can flow back via the tubular extension 12 and the ventilation/overflow orifice 14 via the still open ventilation connection. If at the end of letting off liquor the projection 19 is released, the closing bar 18, driven by the spring 20, closes the outlet connection 7 again and releases the inlet connection 6.

The means with which the closing bars 15, 18 close the respective connections are preferably quoins, with which the conduits, constructed at least in this section as flexible hose conduits, are squeezed into a corresponding opposite piece and thus closed.

While specific embodiments of the invention have been shown and described in detail to illustrate the inventive principles, it will be understood that the invention may be embodied otherwise without departing from such principles.

I claim:

1. A medical drainage chamber for collecting liquor, the drainage chamber comprising:
   a collecting area defined by an outer wall and configured to collect a body fluid;
   an inlet connection linked to the collecting area and linking the drainage chamber to an intraventricular drainage catheter;
   an outlet connection; and
   a ventilation connection linked to ambient air, wherein the drainage chamber further comprises a spring-loaded first closing element biased in the direction of a first closing position, wherein, in its closing position, the first closing element closes both the inlet connection and the ventilation connection, and an actuating mechanism for displacing the first closing element against the spring tension into an open position in which the first closing element releases the inlet connection and the ventilation connection.

2. A drainage chamber according to claim 1, wherein the inlet connection comprises a pipe conduit which in a position of operation of the drainage chamber, penetrating the outer wall at a lower end of the collecting area, extruded upwards toward a top inside the outer wall surrounding the collecting area, and extruding at the top into the collecting area.

3. A drainage chamber according to claim 2, wherein the ventilation connection is arranged on the outer wall of the drainage chamber located at the top in the position thereof of operation of the drainage chamber and is linked to a tubular extension extruding downwards, the tubular extension reaching into the collecting area at least to a height of a mouth of the pipe conduit, and wherein a closing bar, arranged transversely in the collecting area and biased by a spring into a closing position, is provided as the first closing element, which, on actuation, at the same time releases or closes the pipe conduit and the tubular extension.

4. A drainage chamber according to claim 1, wherein the ventilation connection is provided, at its link to ambient air, with a filter which is permanently integrated in the outer wall.

5. A drainage chamber according to claim 1, wherein the ventilation connection is linked to the outlet connection via a conduit mounted inside the outer wall, and wherein, in the position of operation of the drainage chamber, the conduit is open to the collecting area via a ventilation/overflow orifice located above a maximum filling height of the collecting area.

6. A drainage chamber according to claim 1, wherein the drainage chamber comprises a second closing element, the second closing element being spring-loaded in the direction of a closing position and configured to act on the inlet connection and the outlet connection,
wherein the second closing element is configured, in the closing position, to close the outlet connection and release the inlet connection, and in an open position is settable against the spring loading, releases the outlet connection and closes the inlet connection.

7. A drainage chamber according to claim 6, wherein the outlet connection is arranged on the end of the drainage chamber at the bottom in the position of operation thereof and has an extension reaching into the interior of the collecting area, and
wherein the second closing element is a closing bar spring-loaded in the direction of the closing position, which acts on the extension for closing or releasing thereof.

8. A drainage chamber according to claim 6, wherein the first closing element and also the second element are encapsulated to prevent contact with the body fluid located in the collecting area and/or conducted via the inlet connection or the outlet connection.

9. A drainage chamber according to claim 1, wherein the outer wall is of a transparent, rigid material.

10. A drainage chamber according to claim 1, wherein the outer wall is coated on an inner side adjoining the collecting area with a germicidal material.

11. A drainage chamber according to claim 10, wherein the germicidal material is silver oxide.

12. A drainage chamber according to claim 1, wherein the first closing element has an actuating device which is arranged such that, when the drainage chamber is suspended in a receptacle the actuating device displaces the first closing element against the spring force into the open position in which the inlet connection and the ventilation connection are released.

13. A drainage chamber according to claim 11, in combination with a receptacle for the drainage chamber, wherein the receptacle has an engagement face for the actuating element which forces the actuating element to displace the first closing element into the open position, when the drainage chamber is inserted into the receptacle.

* * * * *